United States Patent [19]

Nardi et al.

[11] Patent Number: 4,940,711
[45] Date of Patent: Jul. 10, 1990

[54] ANTIHYPERTENSIVE N-PIPERAZINYLALKANOYLANILIDES

[75] Inventors: Dante Nardi; Amedeo Leonardi; Alberto Catto; Gabriele Graziani, all of Milan, Italy

[73] Assignee: Recordati, S.A., Chemical and Pharmaceutical Company, Chiasso, Switzerland

[21] Appl. No.: 373,451

[22] Filed: Jun. 30, 1989

Related U.S. Application Data

[63] Continuation of Ser. No. 578,374, Feb. 8, 1984, abandoned.

[30] Foreign Application Priority Data

Feb. 12, 1983 [GB] United Kingdom ............... 8303946

[51] Int. Cl.$^5$ .................. A61K 31/495; C07D 295/10
[52] U.S. Cl. ...................................... 514/255; 544/393
[58] Field of Search ....................... 544/393; 514/255

[56] References Cited

FOREIGN PATENT DOCUMENTS 120558   3/1984  European Pat. Off.
912788  12/1962  United Kingdom.
1166595 10/1969  United Kingdom.

Primary Examiner—Cecilia Shen
Attorney, Agent, or Firm—Burns, Doane, Swecker & Mathis

[57] ABSTRACT

N-piperazinylalkanoylanilides of the formula

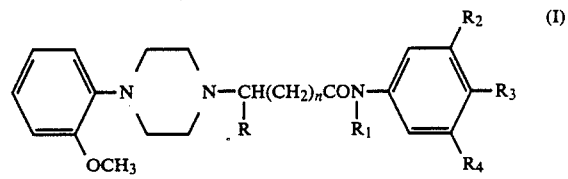

wherein n is 0, 1 or 2, each of R and $R_1$ is H or alkyl, and each of $R_2$, $R_3$ and $R_4$ is H, halogen, alkyl, hydroxyalkyl, alkoxy, aralkoxy, alkylthio, aralkylthio, alkylsulphonyl, alkylsulphenyl, $NO_2$, $NH_2$, alkylamino, acylamino, ureido, alkylureido, alkylsulphonylamino, $CF_3$, acyl, CN, COOH, alkoxycarbonyl, $NH_2CO$, $SO_3H$, guanidinosulphonyl, carbamoyloxy, OH, acyloxy, alkylsulphonyloxy, alkylenedioxy or $SO_2NR_5R_6$ wherein each of $R_5$ and $R_6$ is H, alkyl, aryl or acyl and their pharmaceutically acceptable acid addition salts, are antihypertensive agents.

16 Claims, No Drawings

ANTIHYPERTENSIVE N-PIPERAZINYLALKANOYLANILIDES

This application is a continuation of application Ser. No. 578,374, filed Feb. 8, 1984, now abandoned.

SUMMARY OF THE INVENTION

The present invention relates generally to N-piperazinylalkanoylanilides and nontoxic pharmaceutically acceptable salts thereof, to processes for their production and pharmaceutical compositions and methods of treating hypertension employing same.

It is, therefore, a primary object of the present invention to afford novel substituted N-piperazinylalkanoylanilide compounds which possess antihypertensive activity.

It is a further object of the present invention to provide methods for obtaining antihypertensive effects in mammals by the administration of preselected dosages of active substituted anilide compounds or pharmaceutically acceptable salts thereof in appropriate nontoxic pharmaceutical dosage unit forms or compositions.

A still further object of the present invention is to provide dosage unit forms adapted for, e.g., oral, rectal, parenteral, etc., administration and useful in the treatment, management and mitigation of hypertensive conditions or disorders.

These and other similar objects, advantages and features are accomplished according to the products, compositions and methods of the invention comprised of novel substituted N-piperazinylalkanoylanilides, compositions derived therefrom and antihypertensive methods employing same.

DESCRIPTION OF THE PREFERRED EMBODIMENTS

In accordance with the objects and practices of the present invention, antihypertensively active N-piperazinylalkanoylanilides of the general formula I and pharmaceutically acceptable nontoxic salts thereof are provided:

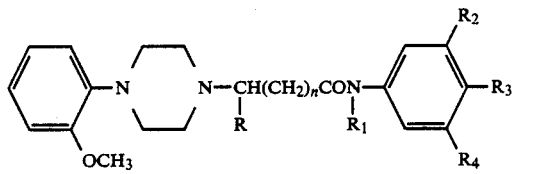

wherein n is 0, 1 or 2, each of R and $R_1$ independently represents a hydrogen atom or an alkyl group, and each of $R_2$, $R_3$ and $R_4$ independently represents hydrogen, halogen, alkyl, hydroxyalkyl, alkoxy, aralkoxy, alkylthio, aralkylthio, alkylsulphonyl, alkylsulphenyl, nitro, amino, alkylamino, acylamino, ureido, alkylureido, arylureido, alkylsulphonylamino, trifluoromethyl, acyl, cyano, carboxy, alkoxycarbonyl, carbamoyl, sulpho, guanidinosulphonyl, carbamoyloxy, hydroxy, acyloxy, alkylsulphonyloxy or alkylenedioxy group, or a group of the formula $SO_2NR_5R_6$ in which each of $R_5$ and $R_6$ independently represents a hydrogen atom or an alkyl, aryl or acyl group.

The terms "alkyl" and "alkoxy" as used herein, whether alone or in combination with another group, refer to such groups having from 1 to 4 carbon atoms which may be straight or branched chain. The term "alkylene", as used herein, refers to a group having from 1 to 4 carbon atoms. The expression "aryl" defines an aromatic ring having 6 to 10 carbon atoms. "Acyl", as used herein refers to a group containing from 1 to 6 carbon atoms. The term "halogen" refers to chlorine, fluorine, bromine and iodine. Also provided by the present invention is a process for the preparation of the N-piperazinylalkanoylanilides of the general formula I as above defined, the process comprising reacting a compound of the general formula II

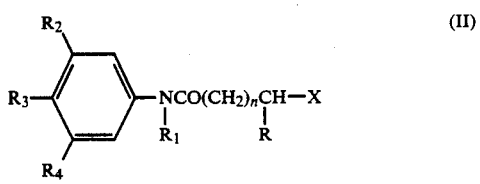

in which R, $R_1$, $R_2$, $R_3$, $R_4$ and n have the meanings given above and X represents a halogen atom, with 1-(2-methoxyphenyl)-piperazine.

An alternative process for the preparation of the N-piperazinylalkanoylanilides of the general formula I in which n is 1 and R, $R_1$, $R_2$, $R_3$, and $R_4$ are as above defined, also within the scope of the invention, comprises reacting a compound of the general formula III

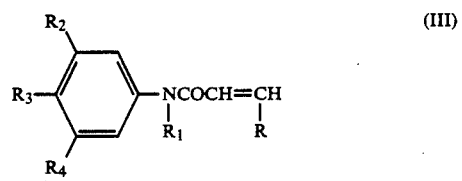

in which R, $R_1$, $R_2$, $R_3$ and $R_4$ have the meanings given above, with 1-(2-methoxyphenyl)-piperazine.

Both of the foregoing reactions are carried out in the presence of a solvent, such as a ketone, a hydrocarbon, dimethylsulphoxide or a mixture thereof. When using dimethylsulphoxide, a reaction temperature of from 40° to 60° C. is sufficient; in other cases the reflux temperature of the solvent is preferred. The compounds thus obtained may be purified according to methods known per se, and crystallized or recrystallized from suitable solvents in purified form.

The pharmaceutically acceptable salts according to the invention may be prepared from the bases in a conventional manner. Preferred pharmaceutically acceptable acid addition salts are those of hydrochloric, sulphuric, maleic, succinic, citric, methanesulphonic and toluenesulphonic acids.

The N-piperazinylalkanoylanilides and their salts according to the invention possess valuable antihypertensive activity and a very low toxicity. Accordingly, the invention also provides pharmaceutical compositions comprising a compound of the general formula I as above defined or a pharmaceutically acceptable salt thereof in admixture with a pharmaceutically acceptable nontoxic inert diluent or carrier.

In accordance with the practices of the present invention, the N-piperazinylalkanoylanilides of the invention may be administered in admixture with suitable pharmaceutical diluents, carriers or other excipients (collectively referred to as "pharmaceutical carrier" materials) suitably selected with respect to the intended route of administration and conventional pharmaceutical practices. For instance, for oral administration in the form of tablets or capsules, the active drug components may be combined with any oral nontoxic pharmaceutically acceptable inert carrier such as lactose, starch, sucrose, cellulose, magnesium stearate, dicalcium phosphate, calcium sulfate, mannitol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, etc. Disintegrators include, without limitation, starch, methylcellulose, agar, bentonite, guar gum, etc. Sweetening and flavoring agents and preservatives can also be included where appropriate. Similarly injectable dosage units may be utilized to accomplish intravenous, intramuscular or subcutaneous administration and, for such parenteral administration, suitable sterile aqueous or non-aqueous solutions or suspensions, optionally containing appropriate solutes to effectuate isotonicity, will be employed. In such compositions, the active compounds of formula (I) will generally comprise between about 1% to 70% by weight of the total composition.

The compounds of the invention or compositions thereof may be administered to warm-blooded mammals, including humans. Dosages sufficient to elicit the above-indicated antihypertensive response will generally range between about 5 to 150 mg/kg/day in laboratory rats based on body weight and, preferably between about 5 to 150 mg/kg/day. The foregoing dosages will normally be administered in three to four divided doses, depending upon the desired dosage regimen. Of course, the actual effective dosage to be administered will vary, depending upon the specific compound involved, as well as the age, weight and responsiveness of the particular animal species.

The LD$_{50}$ of the compounds according to the invention was determined in the mouse per os following the method described by C. S. Weil (Biometrics, 8, 249, 1952). The results obtained are reported below.

In the following Table I, the numbers under AC (active compound) indicate the compounds described in the corresponding Examples (thus "1" indicates the compound prepared in Example 1).

Antihypertensive activity was evaluated in male spontaneously hypertensive rats (SHR, Wister-Kyoto strain, 15–25 weeks old). The determination of blood pressure was performed by the indirect method (M. Gerald et al, Arzneim.-Forsch., 18, 1825, 1968). The animals were prewarmed in a heating chamber at a temperature from 35° to 37° C. for a period of 15 minutes before administering the compounds. The compounds tested by the oral route were dissolved or suspended in a 0.5% methylcellulose solution. Controls were given only the vehicle. Systolic blood pressure and heart rate were measured 1, 3, 5 and 7 hours after drug administration by means of a tail-cuff and the pulse pick-up method using a recorder.

In the Table I, the antihypertensive activity was expressed as ED$_{25}$, which is the drug dose producing a 25% decrease in systolic blood pressure in conscious spontaneously hypertensive rats. The ED$_{25}$ was calculated from the linear regression of the dose-response curve. The tested compounds did not show any significant variation effect on the heart rate.

TABLE I

| AC | LD$_{50}$ (mg/Kg)$^a$os | ED$_{25}$ (mg/Kg)$^a$os |
|---|---|---|
| 2 | >3000 | 7.5 |
| 4 | >3000 | 8.1 |
| 5 | >3000 | 54.5 |
| 6a | 2200 | 58.5 |
| 6b | 1600 | 48.8 |
| 6c | >3000 | 10.0 |
| 6d | 649 | 69.0 |
| 6f | 320 | 17.2 |
| 7 | 2100 | 50.5 |
| 8a | 1000 | 70.2 |
| 9 | 537 | 69.0 |
| 10 | >3000 | 8.7 |
| 11 | >3000 | 100.0 |
| 12 | >3000 | 100.0 |
| 13 | >3000 | 100.0 |
| 14 | >3000 | 100.0 |
| 19 | 340 | 100.0 |
| 20 | 730 | 60.0 |
| 21 | >3000 | 60.0 |

$^a$all compounds were tested as the hydrochloride salt, except for AC 2, 4 and 9 (tested as free bases)

EXAMPLE 1

4-Sulphamoyl-$\gamma$-[4(2-methoxyphenyl)-1-piperazinyl]-butyrylanilide (I: R=R$_1$=R$_2$=R$_4$=H, R$_3$=NH$_2$SO$_2$, n=2)

2.61 g of sodium carbonate and 4.8 g of 1-(2-methoxyphenyl)-piperazine dissolved in 25 ml of acetone were added to 6.9 g of 4-sulphamoyl-$\gamma$-chloro-butyrylanilide in 25 ml of acetone. The whole was refluxed for 32 hours. At the end of the reaction, the solid thus formed was removed by filtration and discarded The solvent was evaporated off in vacuo and the oily residue was treated with diethyl ether until a solid was obtained This solid was collected, dried and suspended in ethanol Hydrogen chloride in ethanol was added until the pH was acidic. The product thus obtained was collected and crystallized first from 90% ethanol and then from methanol to give the title compound as its hydrochloride Yield 3.82 g (32%), mp 235–237° C.

EXAMPLE 2

4-Methylsulphonyl-$\beta$-[4-(2-methoxyphenyl)-1-piperazinyl]-propionylanilide (I: R=R$_1$=R$_2$=R$_4$=H, R$_3$=CH$_3$SO$_2$, n=1)

2.02 g of 4-methylsulphonyl-acryloylanilide and 1.92 g of 1-(2-methoxyphenyl)-piperazine in 20 ml of toluene were refluxed for 4 hours At the end of the reaction, after cooling, the solid thus formed was collected, dried and crystallized from 95% ethanol. After a long drying in vacuo at 100° C., 2.92 g (78%) of the title compound, melting at 142–143° C., was obtained.

EXAMPLE 3

4-Carboxy-$\beta$-[4-(2-methoxyphenyl)-1-piperazinyl]-propionylanilide (I: R=R$_1$=R$_2$=R$_4$=H, R$_3$=COOH, n=1)

3.82 g of 4-carboxy-acryloylanilide and 4.52 g of 1-(2-methoxyphenyl)-piperazine in 20 ml of dimethyl sulphoxide were stirred at 50° C. for 10 hours. At the end of the reaction, the solution was cooled and poured into 100 ml of water. The precipitate thus formed was collected and dried. The crude product was dissolved in ethanol and hydrogen chloride in ethanol was added until the pH was acid. The title compound, as its hydrochloride, was collected, dried and crystallized first from water and then from 95% ethanol.

Yield 4.86 g (57%), mp 234–236° C.

EXAMPLE 4
4-Sulphamoyl-β-[4-(2-methoxyphenyl)-1-piperazinyl]-propionylanilide (I: R=$R_1$=$R_2$=$R_4$=H, $R_3$=$NH_2SO_2$, n=1)

A mixture comprising 2.26 g of 4-sulphamoyl-acryloylanilide and 2.01 g of 1-(2-methoxyphenyl)-piperazine in 60 ml of toluene was refluxed under stirring. After 8 hours, thin layer chromatography showed no starting materials. The crude product was collected, dried and crystallized from dioxane:water. 2.08 g (46%) of the title compound, as its dihydrate, melting at 180–181° C., was obtained. The product was suspended in hot ethanol and hydrogen chloride in ethanol was added until the pH was acid. After cooling the solid was collected and crystallized from water to give the hydrochloride hydrate, mp 237–239° C.

EXAMPLE 5
4-Carbamoyl-β-[4-(2-methoxyphenyl)-1-piperazinyl]-propionylanilide (I: R=$R_1$=$R_2$=$R_4$=H, $R_3$=$NH_2CO$, n=1)

A mixture comprising 1.9 g of 4-carbamoyl-acryloylanilide and 2.01 g of 1-(2-methoxyphenyl)-piperazine in 30 ml of dimethylsulphoxide was stirred for 8 hours at 50–60° C. The mixture was then poured in 150 ml of water and the solid thus precipitated was collected and crystallized from methanol diethyl ether. The title compound was obtained. mp 235–237° C., yield 2.88 g (75%).

The corresponding hydrochloride, mp 246–249° C., was obtained as described in Example 4.

EXAMPLE 6
4-Ethoxycarbonyl-β-[4-(2-methoxyphenyl)-1-piperazinyl]-propionylanilide (I: R=$R_1$=$R_2$=$R_4$=H, $R_3$=$COOC_2H_5$, n=1)

Operating as described in Example 4, but using 2.2 g of 4-ethoxycarbonyl-acryloylanilide in place of the 4-sulphamoyl-acryloylanilide, the title compound was obtained. The product was crystallized from diethyl ether:petroleum ether.

Yield 3.3 g (80%), mp 82–83° C., hydrochloride mp 211° C.

Using the appropriate acryloylanilide derivatives and the conditions and process steps as described in Example 4, the following compounds were obtained:

(a) 4-acetyl-β-[4-(2-methoxyphenyl)-1-piperazinyl]-propionylanilide, mp 138–140° C., crystallized from ethyl acetate, yield 77%. The corresponding hydrochloride melted at 232° C.

(b) 3-trifluoromethyl-β-[4-(2-methoxyphenyl)-1-piperazinyl]-propionylanilide hydrochloride, mp 215–217° C., crystallized from water (yield 87%).

(c) 4-methoxy-β-[4-(2-methoxyphenyl)-1-piperazinyl]-propionylanilide, mp 157–160° C., crystallized from ethyl acetate, yield 81%. The corresponding hydrochloride melted at 210–211° C.

(d) 3-methoxy-β-[4-(2-methoxyphenyl)-1-(piperazinyl]-propionylanilide hydrochloride, mp 214–215° C., crystallized from water (yield 82%).

(e) 4-methylthio-β-[4-(2-methoxyphenyl)-1-piperazinyl]-propionylanilide; yield 75%, mp 165–166° C., crystallized from ethyl acetate. The corresponding hydrochloride hemihydrate melted at 210–211° C.

(f) 4-cyano-β-[4-(2-methoxyphenyl)-1-piperazinyl]-propionylanilide; yield 88%, mp 145–147° C., crystallized from ethyl acetate. The corresponding hydrochloride melted at 211–213° C.

EXAMPLE 7
4-Nitro-β-[4-(2-methoxyphenyl)-1-piperazinyl]-propionylanilide (I: R=$R_1$=$R_2$=$R_4$=H, $R_3$=$NO_2$, n=1)

13.44 g of 4-nitro-acryloylanilide and 13.44 g of 1-(2-methoxyphenyl)-piperazine in 140 ml of toluene were refluxed under stirring for 16 hours. After cooling, the crude product which crystallized out was collected and recrystallized from toluene. 18.81 g (70%) of the title compound, melting at 131–132° C., were obtained. The corresponding hydrochloride melted at 226–227° C.

EXAMPLE 7a
4-Amino-β-[4-(2-methoxyphenyl)-1-piperazinyl]-propionylanilide (I: R=$R_1$=$R_2$=$R_4$=H, $R_3$$NH_2$, n=1)

9.61 g of the free base obtained in Example 7, suspended in 300 ml of methanol, was hydrogenated under pressure in the presence of 0.25 g of palladium-on-charcoal. The catalyst was then removed by filtration, the solvent was evaporated off and the residue was crystallized from ethanol. The title compound was obtained. Yield 8.24 g (93%), mp 124–127° C.

The corresponding bis hydrochloride monohydrate melted at 225–227° C.

EXAMPLE 8
4-Nitro-α-[4-(2-methoxyphenyl)-1-piperazinyl]]-acetanilide (I: R=$R_1$=$R_2$=$R_4$=H, $R_3$=$NO_2$, n=o)

12.46 g of 1-(2-methoxyphenyl)-piperazine in 75 ml of acetone was added to 13.95 g of 4-nitro-α-chloroacetanilide and 5.47 g of sodium bicarbonate in 75 ml of acetone. The whole was refluxed under stirring for 8 hours. At the end of the reaction, 20 ml of chloroform was added in order to maintain in solution all the organic product, and the inorganic salts were removed by filtration. The solvent was evaporated off in vacuo and the residue was crystallized from ethyl acetate:hexane to give 18 g (74%) of the title compound, mp 148–149° C. The corresponding hydrochloride melted at 232–233° C. Following the procedure described in Example 7a for the hydrogenation, the corresponding 4-amino derivative was obtained as its dihydrochloride.

Yield 78% (compound 8a in the Table), mp 262–265° C.

EXAMPLE 9
4-(1Hydroxyethyl)-β-[4-(2-methoxyphenyl)-1-piperazinyl]-propionylanilide (I: R=$R_1$=$R_2$=$R_4$=H, $R_3$=$CH_3CHOH$, n-1)

1.14 g of sodium borohydride were slowly added to 11.44 g of the compound of Example 6a in 200 ml of ethanol. The whole was stirred at room temperature for 8 hours. The solution thus formed was then acidified with dilute hydrochloric acid and subsequently neutralized with aqueous sodium carbonate. The ethanol was evaporated off in vacuo and the aqueous phase alkalinized with aqueous sodium carbonate and then extracted with chloroform. The organic layers were dried on calcium chloride and the solvent was evaporated off in vacuo. The oily residue was purified on a silica gel column using a chloroform:methanol (97:3 by volume) mixture as eluent. The solvent was evaporated off and the residue was crystallized from toluene to give 5.61 g (48%) of the title compound, melting at 137–138° C.

EXAMPLE 10
4-Sulphamoyl-β-[4-(2-methoxyphenyl)-1-piperazinyl]-butyrylanilide (I: R=CH$_3$, R$_1$=R$_2$=R$_4$=H, R$_3$=NH$_2$SO$_2$, n-1)

Operating as described in Example 3, but employing 7.2 g of 4-sulphamoyl crotonylanilide and 6.33 g of 1-(2-methoxyphenyl)-piperazine, stirring for 6 hours, and crystallizing from ethanol, 6.16 g of the title compound, melting at 183–184° C., were obtained.

EXAMPLE 11
4-Acetylsulphamoyl-β-[4-(2-methoxyphenyl)-1-piperazinyl]-propionylanilide (I: R=R$_1$=R$_2$=R$_4$=H, R$_3$=CH$_3$CONHSO$_2$, n=1)

10.73 g of a raw 4-acetylsulphamoyl-acryloylanilide and 8.80 g of 1-(2-methoxyphenyl)-piperazine were stirred for 3 days at room temperature with 40 ml of dimethylsulphoxide. The reaction was then carried out as described in Example 3, obtaining 9.24 g of the title compound.

mp 193–195° C. (crystallization from ethanol).

EXAMPLE 12
4-Acetylamino-β-[4-(2-methoxyphenyl)-1-piperazinyl]-propionylanilide (I: R—R$_1$=R$_2$=R$_4$=H, R$_3$=CH$_3$CONH, n=1)

7.36 g of the compound described in Example 7a and 2.83 ml of acetic anhydride in 40 ml of chloroform were refluxed for 6 hours. At the end of the reaction the solvent was evaporated off under vacuum and the residue treated with dilute sodium bicarbonate until pH 6–7. The solid thus formed was collected, washed with water, dried and crystallized from ethanol.

Yield: 6.18 g of the desired product, mp 200–202° C.

EXAMPLE 13
3-Sulphamoyl-β-[4-(2-methoxyphenyl)-1-piperazinyl]-propionylanilide hydrate (I: R=R$_1$=R$_3$=R$_4$=H, R$_2$=NH$_2$SO$_2$, n=1)

6.78 g of 3-sulphamoyl-acryloylanilide and 6.60 g of 1-(2-methoxyphenyl)-piperazine in 120 ml of toluene were refluxed under stirring for 12 hours. At the end of the reaction, after cooling, the solid thus formed was collected, dried and crystallized twice from 70% ethanol.

Yield 9.5 g of the title compound melting at 118–124° C.

EXAMPLE 14
3-Chloro-β-[4-(2-methoxyphenyl)-1-piperazinyl]-propinylanilide (I: R=R$_1$=R$_3$=R$_4$=H, R$_2$=Cl, n=1)

7.63 g of 3,β-dichloropropionylanilide and 7.4 g of 1-(2-methoxyphenyl)-piperazine in 60 ml of toluene were refluxed under stirring for 5 hours. At the end of the reaction a 10% excess of 1-(2-methoxyphenyl)-piperazine was added and the whole was again refluxed for 4 hours.

At the end of the reaction the mixture was cooled and the solid collected. The solvent was evaporated from the mother liquors under vacuum and the residue, dissolved in ethanol, was treated with hydrogen chloride in ethanol until the pH was acid. The solid was then collected, washed with ethanol and added to the solid obtained in the first filtration. This product was then treated with a solution of sodium bicarbonate until basic pH and extracted with chloroform. The organic layer was separated, dried and the solvent evaporated off.

The oily residue, treated with hexane, crystallized after standing for a long time and was recrystallized from ether.

Yield 5.51 g of the title compound, mp 92–93° C.

EXAMPLE 15
4-Methylsulphamoyl-β-[4-(2-methoxyphenyl)-1-piperazinyl]-propionylanilide (I: R=R$_1$=R$_2$=R$_4$=H, R$_3$=CH$_3$NHSO$_2$, n=1)

To 13.8 g of 4-methylsulphamoyl-β-chloro-propionylanilide in 100 ml of acetone, 5.3 g of sodium carbonate and 10.57 g of 1-(2-methoxyphenyl)-piperazine in 100 ml of acetone were added under stirring. The mixture was refluxed for 9 hours and the solid thus formed collected by filtration. The solvent was then evaporated off giving 13.74 g (from ethanol) of the title compound. mp 168–169° C.

EXAMPLE 16
4-Phenylsulphamoyl-β-[4-(2-methoxyphenyl)-1-piperazinyl]-propionylanilide (I: R=R$_1$=R$_2$=R$_4$=H, R$_3$=PhNHSO$_2$, n=1)

Operating as described in Example 15, but employing 16.9 g of 4-phenylsulphamoyl-β-chloro-propionylanilide, refluxing for 20 hours, and crystallizing from methanol, 14.88 g of the desired compound were obtained. mp 197–201° C.

EXAMPLE 17
4-Guanidinosulphonyl-β-[4-(2-methoxyphenyl)-1-piperazinyl]-propionylanilide (I: R=R$_1$=R$_2$=R$_4$=H, R$_3$=guanidinosulphonyl, n=1)

The reaction was carried out as described in Example 15, but employing 9.14 g of 4-guanidinosulphonyl-β-chloro-propionylaniline, 6.35 g of the piperazine derivative, 3.15 g of sodium carbonate and 75 ml of acetone. Reflux was carried on for 13 hours, then an excess of piperazine derivative (0.58 g) was added, and the mixture was refluxed for another 13 hours. Yield: 6.84 g (from ethanol).

EXAMPLE 18
4-Chloro-3-sulphamoyl-β-[4-(2-methoxyphenyl)-1-piperazinyl]-propionylanilide (I: R=R$_1$=R$_4$=H, R$_2$=Cl, R$_3$=SO$_2$NH$_2$, n=1)

The reaction was carried out as described in Example 14, but employing 5.94 g of 4,β-dichloro-3-sulphamoyl-propionylanilide, 30 ml of acetone, 2.10 g of sodium carbonate and 4.21 g of the piperazine derivative in 30 ml of acetone. Reflux was for 18 hours, without excess of the piperazine derivative. The residue obtained from mother liquirs was treated with ethyl acetate until a precipitate was obtained, and this was added to the first precipitate. The solid mixture was crystallized from dioxan, giving 6.71 g of the title compound. mp 191–193° C.

EXAMPLE 19
3,4-Methylenedioxy-β-[4-(2-methoxyphenyl)-1-piperazinyl]-propionylanilide (I: R=R$_1$=R$_4$=H, R$_2$+R$_3$=methylenedioxy, n=1)

7.65 g of 3,4-methylenedioxy-acryloyolanilide and 8.40 g of 1-(2-methoxyphenyl)-piperazine in 80 ml of toluene were refluxed for 3 hours under stirring. At the end of the reaction the solvent was evaporated off and the residue treated with ether. The dark solvent was collected by filtration and dissolved in 140 ml of toluene. To the solution were gradually added 300 ml of hexane and a precipitate was obtained. The solution was then decanted, treated with coal and filtered. By cooling, a solid was obtained which was recrystallized from toluene.

Yield 8.1 g, mp 118–120° C.

EXAMPLE 20
3,4,5-Trimethoxy-β-[4-(2-methoxyphenyl)-1-piperazinyl]-propionylanilide hydrochloride (I: R=R₁=H, R₂=R₃=R₄=methoxy, n=1)

The reaction was carried out as described in Example 2, using 5.69 g of 3,4,5-trimethoxy-acryloylanilide, 5.07 g of the piperazine derivative and 50 ml of solvent. Reflux 5 hours, crystallization from ethyl acetate.

Yield 6.48 g, mp 119–122° C.

The free base was treated with hydrogen chloride in ethanol giving the corresponding hydrochloride.

Yield 5.45 g, mp 235–237° C.

EXAMPLE 21
4-(Dimethylsulphamoyl)-β-[4-(2-methoxyphenyl)-1-piperazinyl]-propionylanilide (I: R=R₁=R₂=R₄=H, R₃=SO₂N(CH₃)₂, n=1)

Operating as described in Example 15, but employing 7.28 g of 4-(dimethylsulphamoyl)-β-chloro-propionylanilide, 2.64 g of sodium carbonate, 5.26 g of the piperazine derivative and 70 ml of acetone (reflux 10 hours), 8.35 g of the title compound were obtained (from dioxan). mp 178–179° C.

EXAMPLE 22
4-Sulpho-β-[4-(2-methoxyphenyl)-1-piperazinyl]-propionylanilide (I: R=R₁=R₂=R₄=H, R₃=SO₃H, n=1)

The reaction was carried out as described in Example 15, but employing 6.32 g of 4-sulpho-β-chloro-propionylanilide, 40 ml of dimethylformamide as solvent, 2.56 g of sodium carbonate and 5.03 g of the piperazine derivative (100° C., 8 hours). The solid was suspended in water, brought to pH 4 with water acetic acid, collected by filtration, washed with water to free from sodium ions and dried.

Yield 7.77 g, mp 310–313° C.

While the invention has been described and illustrated with reference to certain preferred embodiments thereof, those skilled in the art will appreciate that various changes, modifications and substitutions can be made therein without departing from the spirit of the invention. For example, effective dosages other than the preferred ranges set forth hereinabove may be applicable as a consequence of variations in the responsiveness of the mammal treated, severity and origin of hypertension, dosage related adverse effects, if any, observed and analogous considerations. Likewise, the specific pharmacological responses observed may vary depending upon the particular relative amounts of active components employed or whether same are used in combination with suitable pharmaceutical carriers, as well as the type of formulation and mode of administration employed, and such expected variations or differences in results are contemplated in accordance with the objects and practices of the present invention. It is intended, therefore, that the invention be limited only by the scope of the claims which follow.

What is claimed is:

1. An N-piperazinylalkanoylanilide having the formula I or a pharmaceutically acceptable non-toxic salt thereof:

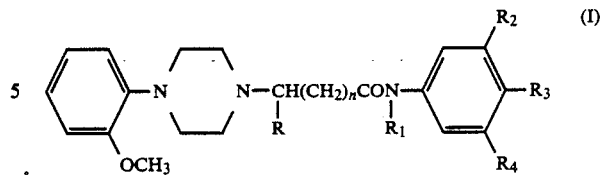

wherein n is 0, 1 or 2; R represents a hydrogen atom or an alkyl group; R₁ represents a hydrogen atom; one of R₂ and R₃ represents a hydrogen atom and the other of R₂ and R₃ represents a hydroxyalkyl, alkylthio, alkylsulphonyl, alkylsulphonyl, alkanoyl, carbamoyl or guanidinosulphonyl group; or a group of the formula SO₂NR₅R₆ in which each of R₅ and R₆ independently represents a hydrogen atom or an alkyl, phenyl or alkanoyl group; or one of R₂ and R₃ represents a halogen atom and the other of R₂ and R₃ represents a sulphamoyl group; and R₄ is a hydrogen atom; said alkyl group having from 1 to 4 carbon atoms.

2. The N-piperazinylalkanoylanilide according to claim 1 wherein n is 1, each of R and R₂ represents a hydrogen atom, and R₃ represents a carbamoyl, acetyl, methylthio, 1-hydroxyethyl, acetylsulphamoyl, methylsulphamoyl, phenylsulphamoyl, guanidinosulphonyl or dimethylsulphamoyl group.

3. 4-Methylsulphonyl-β-[4-(2-methoxyphenyl)-1-piperazinyl]-propionylanilide.

4. 4-Sulphamoyl-β-[4-(2-methoxyphenyl)-1-piperazinyl]-propionylanilide.

5. 4-Sulphamoyl-β-[4-(2-methoxyphenyl)-1-piperazinyl]butyrylanilide.

6. 4-Acetylsulphamoyl-β-[4-(2-methoxyphenyl)-1-piperazinyl]-propionyl anilide.

7. The N-piperazinylalkanoylanilide according to claim 1 wherein said N-piperazinylalkanoylanilide is 3-sulphamoyl-β-[4-(2-methoxyphenyl)-1-piperazinyl]-propionylanilide.

8. The N-piperazinylalkanoylanilide according to claim 1 wherein said N-piperazinylalkanoylanilide is 4-(dimethylsulphamoyl)-β-[4-(2-methoxyphenyl)-1-piperazinyl]-propionylanilide.

9. The N-piperazinylalkanoylanilide according to claim 1 wherein said N-piperazinylalkanoylanilide is 4-methylthio-β-[4-(2-methoxyphenyl)-1-piperazinyl]-propionylanilide.

10. The N-piperazinylalkanoylanilide according to claim 1 wherein said N-piperazinylalkanoylanilide is 4-methylsulphamoyl-β-[4-(2-methoxyphenyl)-1-piperazinyl-propionylanilide.

11. The N-piperazinylalkanoylanilide according to claim 1 wherein said N-piperazinylalkanoylanilide is 4-chloro-3-sulphamoyl-β-[4-(2-methoxyphenyl)-1-piperazinyl]-propionylanilide.

12. The N-piperazinylalkanoylanilide according to claim 1 wherein said N-piperazinylalkanoylanilide is 4-sulphamoyl-3-chloro-β-[4-(2-methoxyphenyl-1-piperazinyl]-propionylanilide.

13. The N-piperazinylalkanoylanilide according to claim 1 wherein said N-piperazinylalkanoylanilide is 4-methylsulphonyl-β-[4-(2-methoxyphenyl)-1-piperazinyl]-propionylanilide.

14. A pharmaceutical composition comprising an antihypertensively effective amount of the N-piperazinylalkanoylanilide according to claim 1 or a pharmaceutically acceptable salt thereof in admixture with a pharmaceutically acceptable diluent or carrier.

15. A method of promoting an antihypertensive effect in a warm-blooded animal in need thereof comprising administering thereto an antihypertensively effective amount of the N-piperazinylalkanoylanilide according to claim 1.

16. The method according to claim 15 wherein said N-piperazinylalkanoylanilide is 4-methylsulphonyl-β-[4-(2-methoxyphenyl)-1-piperazinyl]-propionylanilide, 4-sulphamoyl-β-[4-(2-methoxyphenyl)-1-piperazinyl]-propionylanilide, 4-sulphamoyl-β-[4-(2-methoxyphenyl)-1-piperazinyl]butyrylanilide, 4-acetylsulphamoyl-β-[4-(2-methoxyphenyl)-1-piperazinyl]-propionylanilide, 3-sulphamoyl-β-[4-(2-methoxyphenyl)-1-piperazinyl]-propionylanilide, 4-(dimethylsulphamoyl)-β-[4-(2-methoxyphenyl)-1-piperazinyl]-propionylanilide, 4-methylthio-β-[4-(2-methoxyphenyl)-1-piperazinyl]-propionylanilide, 4-methylsulphamoyl-β-[4-(2-methoxyphenyl)-1-piperazinyl]-propionylanilide, 4-chloro-3-sylphamoyl-β-[4-(2-methoxyphenyl)-1-piperazinyl]-propionylanilide 4-sulphamoyl-3-chloro-β-[4-(2-methoxyphenyl)-1-piperazinyl]-propionylanilide or 4-methylsulphonyl-β-[4-(2-methoxyphenyl)-1-piperazinyl]-propionylanilide.

* * * * *